United States Patent [19]

Moore

[11] Patent Number: 5,683,906
[45] Date of Patent: Nov. 4, 1997

[54] PREPARATION OF IMMORTALIZED CELLS

[75] Inventor: Emma E. Moore, Seattle, Wash.

[73] Assignee: ZymoGenetics, Inc., Seattle, Wash.

[21] Appl. No.: 303,983

[22] Filed: Sep. 9, 1994

[51] Int. Cl.$^6$ .............................. C12N 5/06; C12N 5/18; C12N 15/06; C12N 15/09
[52] U.S. Cl. .................. 435/325; 435/172.1; 435/172.3; 435/354; 800/2
[58] Field of Search ........................ 435/240.1, 240.2, 435/240.21, 172.1, 172.3, 325, 354; 800/2

[56] References Cited

FOREIGN PATENT DOCUMENTS

92/11874  7/1992  WIPO.
95/02687  1/1995  WIPO.

OTHER PUBLICATIONS

Bradley et al. 1992. Biotechnology 10: 534–438.
Tsukada et al., *Oncogene* 8: 3313–3322, 1993.
Harvey et al., *Oncogene* 8: 2457–2467, 1993.
Gotoh et al., *Transplantation* 40: 437–438, 1985.
Powers et al., *Diabetes* 39: 406–414, 1990.
Bischoff et al., *Oncogene* 6: 183–186, 1990.
Chiba et al., *Jpn. J Cancer Res.* 84: 290–297, 1993.
Boyce et al., *J. Bone and Min. Res. Abstract* 8: S118, 1993.
Hamaguchi et al., *Diabetes* 40: 842–849, 1991.
Donehower et al., *Nature* 356: 215–221, 1992.
Yanai et al., *Exp. Cell res.* 197: 50–56, 1991.
Jat et al., *Proc. Natl. Acad. Sci. USA*: 88: 5096–5100, 1991.
Chambers et al., *Proc. Natl. Acad. Sci. USA* 90: 5578–5582, 1993.
Lavigueur et al., *Mol Cell. Biol.* 9: 3982–3991, 1989.
Radvanyi et al., *Mol. Cell. Biol.* 13: 4223–4232, 1993.

*Primary Examiner*—Brian R. Stanton
*Attorney, Agent, or Firm*—Deborah A. Sawislak

[57] ABSTRACT

Cell lines have been prepared from growth suppressor gene deficient animals. The cells include immortalized precursor cells and differentiated cells such as osteoclast precursors, osteoblast precursors, megakaryocytes, osteoclasts, osteoblasts, pancreatic α-cells, pancreatic β-cells, pancreatic δ-cells, adipocytes, macrophages, chondrocytes and hepatocytes. The cells are useful for constructing cDNA and protein libraries, screening agonists and antagonists of compounds and factors that affect metabolic pathways of specific cells and generating cell-specific antibodies.

10 Claims, No Drawings

PREPARATION OF IMMORTALIZED CELLS

DESCRIPTION

Cell lines have played an important role in the development of molecular and cellular biology, particularly in the elucidation of intracellular activities, the effects of extracellular molecules and cell-cell interactions. Cell lines are established stepwise by: explantation of tissue containing a heterogeneous cell population; separation of the cells; isolation of a cell clone; and culturing the cell clone so that the total cell number increases over several generations and the population is uniform in its lineage. Cell cultures may be started from primary tissue culture explants, where heterogeneous cell types separate or migrate from the tissue in liquid medium; or by enzyme digestion of a tissue, resulting in dispersed cell suspensions.

Differentiation is the process of maturation of cells. It is a progressive and dynamic process, beginning with pluripotent stem cells and ending with terminally differentiated cells that progress no further down the cell lineage pathway. A cell's function, phenotype and growth characteristics are affected by the cell's degree of differentiation.

Cells that can be continuously cultured are known as immortalized cells. Immortalized cells have advantages over non-immortalized cells because they can be cultured to provide large numbers of uniform cell populations. Immortalized cells are routinely used for understanding intracellular activities such as the replication and transcription of DNA, metabolic processes and drug metabolism. Investigation of cellular transmembrane activities such as ligand-receptor interactions and signal transduction are facilitated by access to specific cell types. Immortalized cells are also useful in the development of an understanding of specific cell-cell interactions such as adhesion, invasion and contact inhibition. However, many cell types have remained recalcitrant to isolation and continuous culture, such as cells of the osteoclast lineage, hematopoietic-CD34$^+$ stem cells, mesenchymal stem cells and other cell precursors that are at early stages of differentiation. In addition, many differentiated cells lose some of their differentiated properties in order to regain or retain the ability to proliferate. Thus many of the available cell lines that can be continuously cultured do not express the differentiation functions that make them valuable tools.

Therefore there remains a need in the art for new methods to immortalize cells and establish cell lines that can be continuously cultured. There also remains a need for certain types of immortalized stem cells, precursor cells and fully differentiated cells that retain their differentiated properties while continuously being cultured.

SUMMARY OF THE INVENTION

It is an object of the present invention to provide methods for preparing immortalized cells from a tissue of a growth suppressor gene deficient animal.

It is a further object of the invention to provide methods for preparing immortalized cells that express a set of differentiation markers not expressed by fibroblast cells.

It is a further object of the invention to provide immortalized cells, including immortalized cells that express a set of differentiation markers not expressed by fibroblast cells.

Another object of the present invention is to provide differentiated cells of a predetermined type, and immortalized cells that can be stimulated to differentiate into cells of the predetermined type.

The methods of the present invention comprise the steps of culturing a tissue from a growth suppressor gene deficient animal in a medium; isolating component cells from the cultured tissue; assaying at least a portion of the isolated cells for expression of a set of differentiation markers characteristic of a cell-type of interest, to identify a subset of said isolated cells, wherein the set of markers is not expressed by fibroblast cells; and selectively culturing cells of said subset of cells to identify an immortalized cell population. Within one embodiment, the portion of the isolated cells is stimulated to differentiate prior to the step of assaying. Within another embodiment, cells of the immortalized population are stimulated to differentiate to provide differentiated cells.

Within one preferred embodiment the growth suppressor gene is p53. Within another preferred embodiment, the tissue is either bone marrow or calvarial bone. Within another preferred embodiment, the cells of the subset of isolated cells are either osteoclast precursors or osteoblast precursors. Within another embodiment the set of differentiation markers is selected from the group consisting of TRAP and calcitonin receptor; ALP, osteocalcin and PTH receptor; cardiac myosin isozyme and cardiac specific creatine kinase isozyme; myosin isozyme and muscle specific creatine kinase isozyme; aggrecan and collagen Type IIB; mpl receptor and acetyl choline; insulin; glucagon and glucagon-like polypeptide; somatostatin; triglyceride and perilipin; NSE and Mac-1; and albumin, liver-specific glucokinase, liver-specific pyruvate kinase and liver isozyme of glycogen synthase.

Within a related aspect of the invention, immortalized cells prepared by the methods disclosed above are provided. In one embodiment the cells are selected from the groups consisting of osteoclast precursors, osteoblast precursors, cardiac muscle precursor cells, skeletal muscle precursor cells, chondrocyte precursors, megakaryocytes, pancreatic α-cell precursors, pancreatic β-cell precursors, adipocyte precursors, macrophages and hepatocyte precursors. Within another embodiment, cells are selected from the group consisting of osteoclasts, osteoblasts, pancreatic α-cells, pancreatic β-cells, pancreatic δ-cells, adipocytes, chondrocytes, macrophages and hepatocytes.

These and other aspects of the invention will become evident upon reference to the following description.

DETAILED DESCRIPTION OF THE INVENTION

As noted above, the present invention provides methods for preparing immortalized cells. The methods comprise the steps of culturing a tissue from a growth suppressor gene deficient animal in a medium; isolating component cells from the cultured tissue; assaying at least a portion of the isolated cells for expression of a set of differentiation markers characteristic of a cell type of interest to identify a subset of said isolated cells, wherein the set of differentiation markers is not expressed by fibroblast cells; and selectively culturing cells of said subset of cells, wherein said subset of cells is immortalized.

The present invention provides methods of obtaining immortalized cell lines and differentiated cells from a variety of animals, including mammals, birds, fish, insects, reptiles and amphibians. Of particular interest are mammals, including primates; laboratory animals such as rats, mice, rabbits and dogs; and livestock animals such as horses, cows, swine and fowl.

Cells that can be continuously cultured and do not die out after a limited number of cell generations are known as "immortalized." A cell that will survive for only 20 to 80 population doublings is considered finite (Freshney, *Culture of Animal Cells*, Wiley-Liss, New York, 1994, herein incorporated by reference), and cells that survive more than 80, preferably at least 100, cell generations are considered immortalized.

Immortalization may be associated with transformation, implying increased tumorigenicity and drastic changes in phenotype, but cells may be immortalized without being tumorigenic. The altered ability to be continuously cultured may be due to, for example, a deletion or mutation in one or more of the genes whose products play a role in cell sensecence, or overexpression or mutation of one or more oncogenes that override the action of the senescence genes. Expression of genes that result in the positive signals for cell proliferation include SV40 large T antigen (Linder et al. *Exp. Cell Res.* 191:1–7, 1990), polyoma large T antigen (Ogris et al., *Oncogene* 8:1277–1283, 1993), adenovirus E1A (Braithwaite et al., *J. of Virol.* 45:192–199, 1983), myc oncogene (Khoobyarian et al., *Virus Res.* 30:113–128, 1993), and the E7 gene of papilloma virus Type 16 (McDougall, *Curr. Top. Microbiol. Immunol.* 186:101–119, 1994). One group of sensecence genes is the tumor or growth suppressor genes. These genes are negative regulators of cell proliferation. Inactivation of growth suppressor genes is generally associated with transformation of cells and often results in tumor formation in vivo. Included in this group are p53, RB, NF1, p16 and DCC genes (Marshall, *Cell* 64:313–326, 1991). Immortalization of cells can occur either spontaneously or be chemically or virally induced.

Animals that are "growth suppressor gene deficient" include those animals that are homozygous for a mutation in a growth suppressor gene resulting in lack of expression of a functional growth suppressor gene product. Such mutations may arise spontaneously or be introduced. Growth suppressor gene deficient animals, such as mice and other species, may be produced, for example, by a process called homologous recombination, in which a mutated DNA sequence seeks its complement on a chromosome and then recombines to replace a portion of the native allele (Baribault et al. *Mol. Biol. Med.* 6:481–492, 1989 and Bernstein et al. *Mol. Biol. Med.* 6:523–530, 1989). Briefly, a DNA sequence encoding a growth suppressor gene is modified to prevent expression of a functional gene product. For example, internal stop codons, deletions, frameshifts or some other modification that would terminate translation can be introduced into the DNA sequence of the growth suppressor gene along with a selectable marker. The modified sequence is transfected into embryonic stem cells, and transfected clones identified by selective pressure are screened to identify those cells that have incorporated the modified gene by homologous recombination. The cells containing the modified DNA sequence are implanted into blastocytes, which are subsequently injected into the uteri of pseudopregnant female mice, and the resulting chimeric animals are subjected to a series of back crosses to identify animals that are homozygous for the modified gene (Robertson, *Biol. of Reproduc.* 44:238–245, 1991). In the alternative, growth suppressor gene deficient animals can be obtained commercially, for example, from DNX (Princeton, N.J.), GenPharm International (Mountain View, Calif.) and The Jackson Laboratory (Bar Harbor, Me.). When the animal contains a growth suppressor gene deficiency that prevents the expression of a growth suppressor gene product, it is referred to as a "knockout" animal.

Growth suppressor genes include RB (Horowitz et al. *Proc. Natl. Acad. Sci. USA* 87:2775–2779, 1990 and Hansen et al., *Trends Genet.* 4:125–128 1988), NF1 (Cawthon et al. *Cell* 62:193–201, 1990), p16 (Marx, *Science* 264:1846, 1994) and p53 genes (Nigro et al. *Nature* 342:705–708, 1989). Other growth suppressor genes may, however, be altered to produce animals with growth suppressor gene mutations (Hiti, *Molec. Cell. Biol.* 9:4722–4730, 1989; Gallie, *J. Cell. Biochem.* 32:215–222, 1986; Alt et al., *Cold Spr. Harb. Symp. Quant. Biol.* 51:931–942, 1986; Malcolm, *Molec. Med.* 1:79–84 1984; all herein incorporated by reference). A particularly preferred growth suppressor gene is p53. The physiological role for p53 appears to be in regulation of the cell cycle. While the precise function of the p53 protein has not been elucidated, it is thought to interact with the large T antigen and possibly be a transactivator of transcription (Donehower et al. *Nature* 356:215–221, 1992). Mutations in p53 have been correlated to increased tumorgenicity, particularly lung carcinomas, osteosarcomas and lymphoid tumors (Lavigueur et al. *Mol. Cell. Biol.* 9:3982–3991, 1989).

In the methods of the present invention a tissue is excised from a growth suppressor gene deficient animal and placed in a culture medium. Tissue is a composite of heterogeneous cell populations. Examples of tissues include bone marrow, bone, skeletal and cardiac muscle, pancreas, brain and liver. Tissues usually consist of a mixture of tissue specific cell-types as well as cells found in many tissues, such as fibroblasts.

Component cells are isolated from tissue by plating cells at a density sufficiently low that colonies grow from a single cell. When necessary, the tissue is disrupted according to conventional enzymatic or mechanical methods to separate component cells. Cell populations originated from a single cell are referred to as clonal colonies or clonal cell populations.

Methods of isolating cells from tissue are known in the art. See, for example, *Methods In Molecular Biol.: Animal Cell Culture*, 5, Pollard et al. eds., Humana Press, New Jersey, 1990, which is incorporated herein by reference. For example, osteoclasts, osteoblasts, macrophages and their precursors may be isolated from bone marrow (for a review, see, for example, Dexter et al., in *Long-Term Bone Marrow Culture*:57–96, Alan R. Liss, 1984). Bone marrow is extracted from a sacrificed animal by dissecting out the femur, removing soft tissue from the bone and cutting off the epiphyses (cortical ends). The bone marrow is removed with a needle and syringe or flushed out with an isotonic solution. The marrow cells are plated at a low density into petri dishes and allowed to attach to the surface of the dish. Clonal colonies are picked and replica plated for continuous culturing and characterization.

Cells of the osteoblast lineage may be isolated from bone. Methods for isolating osteoblasts from bone are known in the art (see, for example, Aubin et al., *J. of Cell Biol.* 92:452–461, 1982). One method of isolation uses calvarial bone. The calvaria is excised, rinsed in a medium and minced with scissors. The minced bone is digested with collagenase for a short period of time in medium. The cells are removed by centrifugation and decanting the supernatant, leaving the bone pieces behind. Fetal calf serum is added to inhibit the collagenase digestion. Cells are plated at a low density in an appropriate growth medium, and clonal cell colonies are cultured in replicate for continuous culture and characterization. The collagenase-treated calvaria can also be placed in culture dishes, and osteoblast cells will migrate or "crawl" out from the bone (Robey et al. *Calcified Tiss. Internat.* 37:453–460, 1985). Osteoblasts may also be removed from cancellous bone. For example, femurs are excised from an animal, marrow is expressed, and the bone is placed in an isotonic solution. The femurs are rinsed several times to remove any remaining marrow and soft tissue. The bones are crushed and digested with collagenase as described previously.

Pancreatic α, β and δ cells may isolated by excision of the pancreas and dissociation of individual cells with collagenase or trypsin digestion (Lacy et al. *Diabetes* 16:35, 1967 and Gotoh et al. *Transplantation* 40:437–438, 1985). Methods for the extraction of adipocytes using collagenase (Rodbell, *J. Biol. Chem.* 5 238:375–380, 1974), isolation of skeletal muscle (Yaffe et al. *Develop. Biol.* 11:300–317, 1965), cardiac muscle (Wolleben et al. *Am. J. Physiol.* 252:E673–E678, 1987) and hepatocytes (Seglen, *J. Toxicol. Environ. Health,* 5:551–560, 1979) are known in the art. Stem cells can also be isolated, and include $CD34^+$ cells, non-human species hematopoietic stem cell equivalents (Heimfeld et al., *Curr. Top. Microbiol. Immunol.* 177:95–105, 1994 and Spangrude et al. *Blood,* 78:1395–1402, 1991) and embryonic stem cells (Robertson, ibid., 1991).

The selection of culture medium is determined by the cells to be isolated and is a matter of routine experimental design and within the ordinary skill in the art. At a minimum, culture media contain a carbon source, a nitrogen source, essential amino acids, vitamins and minerals. Media may also contain such components as growth factors or serum, as required. A preferred growth medium for osteoclasts contains α-MEM (JRH, Lexena, Kans.), a modified MEM (Eagle, *Science* 130:432, 1959) without ribonucleosides or deoxyribonucleosides, fetal calf serum fractionated on a lysine sepharose column to remove the plasminogen, L-glutamine and sodium pyruvate. In another embodiment, the growth medium contains α-MEM (JRH, Lexena, Kans.), 15% fetal calf serum, L-glutamine and sodium pyruvate and supports the growth of osteoblasts.

Additional methods for selective growth of specific cell types include varying the substrate for cell attachment or selective detachment after exposure to trypsin or collagenase (Polinger, *Exp. Cell Res.* 63:78–82, 1970; Owens et al., *J. Natl. Cancer Instit.,* 53:261–269, 1974; Milo et al., *In Vitro* 16:20–30, 1980; Lasfargues, "Human Mammary Tumors", in Kruse et al. (eds) *Tissue Culture Methods and Applications,* Academic Press, New York, 1973; Paul, *Cell and Tissue Culture,* Churchill Livingston, Edinburgh, 1975).

Once a clonal population of cells has been established from the component cells of a tissue, at least a portion of the isolated cells from each clone is assayed and analyzed for a set of differentiation markers that are characteristic of the cell-type of interest.

A set of differentiation markers is defined as one or more phenotypic properties that can be identified and are specific to a particular cell type. Differentiation markers are transiently exhibited at various stages of cell lineage. Pluripotent stem cells that can regenerate without commitment to a lineage express a set of differentiation markers that are lost when commitment to a cell lineage is made. Precursor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products and receptors. In one preferred embodiment the set of differentiation markers is selected from the group consisting of tartrate-resistant acid phosphatase (TRAP) and calcitonin receptor (Suda et al., *Endocrine Rev.* 13:66–80, 1992); alkaline phosphatase (ALP) (Murthy et al. *Calcif. Tissue Int.* 39:185–190, 1986), osteocalcin (Rodan et al., *Crit. Rev. Eukaryot. Gene Expr.* 1:85–98, 1991) and parathyroid hormone (PTH) receptor (Aubin et al. *J. of Cell Biol.* 92:452–461, 1982); cardiac myosin isozyme expression, creatine kinase isozyme expression and insulin and insulin-like growth factor receptors I (Wolleben et al. ibid.); myosin isozyme expression and a cardiac specific pattern of creatine kinase isozyme expression (Yaffe et al. *Develop. Biol.* 15:33–50, 1967 and Richler et al. *Develop. Biol.* 23:1–22, 1970); myosin isozyme expression and a muscle specific pattern of creatine kinase isozyme expression (I and II) (Yaffe et al. *Develop. Biol.* 11:300–317, 1965; Yaffe et al. *Develop. Biol.* 15:33–50, 1967 and Richler et al. *Develop. Biol.* 23:1–22, 1970); aggrecan (Doege et al. *J. Biol. Chem.* 266:894–902, 1991) and collagen Type IIB (Sandell et al. *J. Cell Biol.* 114:1307–1319, 1991); mpl receptor (Souyri et al., Cell 63: 1137–1147, 1990) and acetyl choline (Ravid et al., *J. Cell Biol.* 123: 1545–1553, 1993); insulin (Powers et al., *Diabetes* 39: 406–414, 1990); glucagon and glucagon-like polypeptide (Lacy et al. ibid., Gotoh et al. ibid. and Hamaguchi et al. *Diabetes* 40:842–849, 1991); somatostatin (Williams et al. Somatostatin and Pancreatic Polypeptide in *International Textbook of Diabetes Mellitus,* Alberti et al., eds., 1992); triglyceride and perilipin (Greenberg et al. *J. Biol. Chem.* 266(17):11341–11346, 1991 and Greenberg et al. *Proc. Natl. Acad. Sci.* 90(24):12035–12039, 1993); Ly-6C and Mac-1 (McCormack et al. *J. Immunol.* 151:6389–6398, 1993 and Gordon et al. *Current Opin. in Immunol.* 4(25):25–32, 1992) and non-specific esterase (NSE; Yam et al., *Amer. J. Clin. Path.* 55:283, 1971); and albumin, liver-specific glucokinase, liver-specific pyruvate kinase and the liver isozyme of glycogen synthase (Miller et al. *J. Biol. Chem.* 261:785–790, 1986 and Magnuson, *Diabetes* 39: 523–527, 1990).

TRAP and calcitonin receptor identified in the same cell or clonal population of cells are markers for osteoclasts; ALP, osteocalcin and PTH receptor identified together in a cell or clonal population of cells are markers of differentiation for osteoblasts. Cardiac myosin isozyme expression and the cardiac specific pattern of creatine kinase isozyme expression when identified together are markers for cardiac muscles cells; myosin isozyme expression and a muscle-specific pattern of creatine kinase isozyme expression when identified in a cell or clonal population are markers for skeletal muscle cells; aggrecan and collagen Type IIB identified together are markers for chondrocytes; mpl receptor and acetyl choline are markers for megakaryocytes; insulin production is a marker of differentiation for pancreatic β-cells; glucagon and glucagon-like polypeptide are markers for pancreatic α-cells; somatostatin is a marker for pancreatic δ-cells; triglyceride and perilipin are markers for adipocytes; NSE and Mac-1 are markers of differentiation for monocytic lineage cells that include macrophage and osteoclast precursor cells; and albumin, liver-specific glucokinase, liver-specific pyruvate kinase and the liver isozyme of glycogen synthase are markers for hepatocytes.

Identification of a set of differentiation markers is dependent upon the specific marker(s). For example, TRAP (Janckila et al. *Am. J. Clin. Pathol.* 70:45, 1978, incorporated herein by reference), ALP (Goldberg et al. *Nature* 189:297, 1962, incorporated herein by reference) and NSE (Yam et al., ibid. and Brown, B. in *Hematology: Principles and Procedures:*127–130, Lea and Febiger, Philadelphia, 1984, both incorporated herein by reference) activities are identified by cells metabolizing a stain, whereas insulin, glucagon and somatostatin can be identified using immunocytochemistry where protein expression is detected using labeled antibodies (Radvanyi et al., *Mol. Cell. Biol.* 13:4223–4233, 1993, incorporated herein by reference); calcitonin and PTH receptors can be identified by binding assays using a radiolabeled ligand and assays for cAMP (Aubin et al., *J. Cell Biol.* 92: 452–461, 1982 and Nicholson et al., *J. Clin. Invest.* 78:355–360, 1986, both incorporated herein by reference); and Mac-1 is identified using conjugated antibodies against the cell-surface antigen (Springer et al. *Eur. J. Immunol.* 9:301–306, 1979, incorporated herein by reference).

After a subset of cells expressing a set of markers of interest is identified, a portion of the subset is passaged for at least 80 cell generations, preferably 100 cell generations, to establish that the cells are immortalized. Cells not used to establish that the cell line is immortal and can be passaged for the requisite number of cell generations, may be stored for later use using conventional methods well known to those ordinarily skilled in the art. For example, cells may be frozen in growth medium or serum with 15% dimethylsulfoxide (DMSO) added at a temperature of −80° C. or lower.

Immortalized cells can be stimulated to differentiate and to provide differentiated cells such as osteoblasts, osteoclasts, pancreatic α-cells, pancreatic β-cells, pancreatic δ-cells, adipocytes, macrophages, chondrocytes and hepatocytes. Differentiation is induced by exposing the undifferentiated stem cells or precursor cells to factors that are specific to a particular cell type. For example, osteoclasts are stimulated to differentiate by exposure to vitamin D and dexamethasone. Osteoblasts are induced to differentiate by exposure to retinoic acid, TGF-β or bone morphogenic proteins (BMP).

Once an immortalized cell line has been established, genetic material from the cells may be used to construct cDNA libraries. Methods for preparing cDNA libraries are well known in the art. See, for example, Sambrook et al. *Molecular Cloning: A Laboratory Manual*, 2nd ed., Cold Spring Harbor Laboratory Press, Cold Spring Harbor, N.Y., 1989 and Ausabel et al., eds. Current *Protocols in Molecular Biology*, John Wiley and Sons, Inc. New York, 1987. By selecting cells at various stages of differentiation the biological functions that are associated with a specific stage in the differentiation pathway may identified once a cDNA library is prepared from that cell's mRNA.

The libraries may be used to clone novel factors produced by specific cell types that include differentiation factors, growth hormones and other cytokines. For example, osteoblasts can be used to isolate factors that are involved in osteoclast regulation, fracture repair, calcium homeostasis, mineralization and extracellular matrix deposition.

Cells prepared by the methods of the present invention may also be used to prepare a protein library. A protein library is complementary to the cDNA library. Amino acid sequence information obtained from the protein library enables rapid isolation of cDNAs encoding proteins of interest. The use of protein sequence data to design primers for DNA isolation eliminates problems arising in conventional library preparation methods due to relative mRNA abundance. Coupling of protein and cDNA libraries also facilitates the targeted cloning of sequences of particular interest. A protein library is prepared by extracting protein (total proteins or fractions of interest) from cells according to known methods, then separating the proteins by two-dimensional gel electrophoresis. Isolated proteins are then subjected to in situ tryptic digestion followed by separation by micro-bore HPLC. The separated fragments are then analyzed by mass spectrometry. The resulting mass profile is searched against a protein sequence data base to infer protein identity. Unidentified peptides can be sequenced by Edman degradation. The resulting cDNA and protein libraries are valuable sources of new proteins and the sequences encoding them.

The cells of the present invention may also be used for screening agonists and antagonists of compounds and factors that affect the various metabolic pathways of a specific cell. For example, cells of the osteoclast lineage may be used to screen for molecules that inhibit osteoclast growth or differentiation or inhibit bone resorption itself. In addition, the cells of the present invention may be used to generate antibodies for cell-specific proteins, elucidate the interactions between cell types and cell matrix components and may be used for expressing foreign genes. For example, antibodies to cell-surface markers may be generated and used to purify a subpopulation from a heterogenous population of cells using a cell sorting system. Using membrane fragments from cells of the present invention, monoclonal antibodies are produced according to methods known in the art (Kohler et al. *Nature* 256: 495, 1975; *Eur. J. Immunol.* 6: 511–519, 1976) and Hurrell, J. G. R., ed., *Monoclonal Hybridoma Antibodies: Techniques and Applications*, CRC Press Inc., Boca Raton, Fla., 1982) and screened using a variety of cell lines to identify antibodies that display cell specificity. In addition, cell specific monoclonal antibodies can be used to purify cell-surface markers and identify their function. Stem cells and precursor cells can be marked, for example, using β-galactosidase, and their ontogeny followed in heterogenous cell and nutrient environments.

The invention is illustrated by the following, non-limiting examples.

EXAMPLE I

Preparation of an Osteoclast Precursor Cell Line
A. Harvesting cells from p53 knockout mice Three male p53 knockout mice homozygous were purchased from GenPharm (Mountain View, Calif.). The mice were approximately five weeks old. The mice were sacrificed by cervical dislocation and swabbed with ethanol. The skin was removed from the animals and the femurs dissected out. In a sterile environment, the soft tissue was removed from the bone and the cortical ends cut off, leaving the long bone portion of the femur. Bone marrow was removed from the femur long bone by forcefully expressing the marrow from the medullary cavity using a 26 gauge needle and 10 cc syringe.

The bone marrow was placed in a centrifuge tube in several milliliters of growth medium (Table 1) and spun in a Beckman TJ-6 centrifuge (Beckman Instruments, Palo Alto, Calif.) at 3,000 rpm for 5 minutes. The cells were resuspended in growth medium, counted and plated at a density of $1 \times 10^6$ cells/ml in multiple 10-cm culture dishes (American Scientific Products, Chicago, Ill.).

TABLE 1

500 ml α-MEM (GIBCO BRL, Gaithersburg, MD)
10% fetal calf serum (HyClone, Logan, Utah)
1 mM sodium pyruvate (Irvine, Santa Ana, CA.)
0.29 mg/ml L-glutamine (Hazelton, Lenexa, KS.)

The cells were allowed to attach and grow for 3 days at 37° C. in 5% $CO_2$. After the incubation period, suspension cells were removed by pipetting off spent medium and removing any non-adherent cells. The cells were incubated for approximately one week or until each clone had formed a sizable colony. Each colony was subcloned by harvesting the cells using Sigma NONENZYMATIC ASSOCIATION AGENT (Sigma, St. Louis, Mo.) and plated in duplicate culture dishes, one for maintaining the cell line, and the other for further characterization. One cell line, designated OC10A, was found to have characteristics of osteoclasts when cultured in conditions that promoted differentiation.

B. Characterization of osteoclast phenotype by calcitonin binding assay

The subcloned cells were plated at a density of $5 \times 10^4$ cells/well on an 8-chamber slide (Nunc, Naperville, Ill.) and allowed to grow for 1 week to 10 days at 37° C. and 5% $CO_2$ in 500 μl of growth medium with $10^{-8}$M 1α,25-dihydroxycholecaliferol and $10^{-7}$M dexamethasone added to promote differentiation. The medium was removed, and the cells were washed in PBS. Three hundred microliters of binding medium (RPMI (Fred Hutchinson Cancer Research Center, Seattle, Wash.) and 0.1% BSA) was added to each well. Three hundred microliters of binding medium containing 0.2 nM radiolabeled $^{125}$I salmon calcitonin with a specific activity of approximately 1000 Ci/mmole (Peninsula, Belmont, Calif.) were added to half the wells, and 300 μl of binding medium containing 0.2 nM $^{125}$I salmon calcitonin and 1 μM unlabeled salmon calcitonin were added to the remaining wells. The slides were incubated for 1.5 hours at room temperature, then rinsed 3 times with PBS to remove unincorporated radioactivity. The slides were immediately prepared for TRAP staining.

C. Characterization of osteoclast phenotype by TRAP staining.

Osteoclasts express a tartrate resistant form of acid phosphatase (TRAP). TRAP staining detects cells that are tartrate resistant by formation of an insoluble red stain. Slides that had been treated for calcitonin receptor analysis (example IB) were fixed by adding 100 μl of a solution containing 2.5% glutaraldehyde and 3.5% formaldehyde in PBS for 10 minutes. After the glutaraldehyde/formaldehyde solution was removed, 100 μl of a 1:1 acetone/ethanol solution was added for 1 minute. An Acid Phosphatase, Leukocyte kit (Sigma, St. Louis, Mo.) was used to prepare a substrate solution containing 45 ml of deionized water at 37° C., 1.0 ml of Diazotized Fast Garnet GBC solution (0.5 ml Fast Garnet GBC Base solution and 0.5 ml sodium nitrite solution), 0.5 ml Naphthol AS-BI Phosphate solution, 2.0 ml Acetate solution and 1.0 ml tartrate solution according to the manufacturer's specifications. Approximately 100 μl of the substrate solution was added to each well. The plates were incubated at 37° C. for 30–60 minutes. The stain was removed and the plates were washed gently with tap water. The slides were examined microscopically for TRAP positive cells. After examination the slides were dipped in Kodak NTB3 emulsion (Kodak, Rochester, N.Y.) and allowed to air dry. The slides were placed at 4° C. for 12 days in the dark and developed in Kodak D19 developer (Kodak). After being developed, the slides were fixed in RAPID FIX (Kodak) for 5 minutes. A differentiated subpopulation of clone OC-10 was found to express the calcitonin receptor and tartrate-resistant acid phosphatase.

D. NSE Staining for Identification of Monocyte/Macrophage Lineage

The NSE assay uses specific esterase substrates in defined reaction conditions to distinguish granulocytes from monocytes. Cells of the monocyte lineage include macrophages and osteoclasts. Bone marrow cultures are incubated with alpha-naphthlyl acetate in the presence of a stable diazonium salt. Enzymatic hydrolysis of ester linkages liberates free napthol compounds. The napthol compounds couple with the diazonium salt, forming highly colored deposits at the sites of enzyme activity.

Cells were plated at $5 \times 10^4$ cells/well on an 8-chamber slide (Nunc). The cells were affixed to the slides in Citrate-Acetone-Methanol Fixative for 1 minute at room temperature. The fixative was prepared using 18 ml of citrate dilute solution (0.383M citrate buffer pH 5.4 diluted 1 part citrate buffer to 9 parts deionized water pH 5.4), 27 ml ACS grand acetone and 5 ml methanol. After fixation, the slides were washed thoroughly in deionized water and air dried for at least 20 minutes. A capsule of FAST BLUE RR SALT (Sigma, St. Louis, Mo.) was added to 50 ml of TRIZMAL 7.6 Dilute Buffer Solution (Sigma) in a Coplin jar. One part TRIZMAL 7.6 buffer concentrate is diluted with 9 parts deionized water to make the dilute solution. When the salt was dissolved, 2 ml of alpha-Naphthyl Acetate solution (Sigma) was added and stirred for 15–20 seconds. Specimen slides were added to the jar and incubated for 30 minutes at 37° C. The slides were removed from the stain and washed for 3 minutes in deionized water, air dried and examined microscopically. NSE positive cells were seen in OC10A cultures, with and without the addition of 1α, 25-dihydroxycholecalciferol, indicating the presence of cells of the monocytic lineage.

E. Identification of the Mac-1 Antigen

Mac-1 is a cell surface antigen expressed by monocytes, granulocytes and macrophages, but not by mature osteoclasts. Mac-1 positive cells were identified by using a rat monoclonal antibody to Mac-1 (Boehringer Mannheim, Indianapolis, Ind.).

Cells were prepared on 8 chamber slides as discussed in the previous examples. The wells were rinsed in PBS with 1 mg/ml BSA added and fixed in Z FIX (Anatech Ltd., Battle Creek, Mich.) for 10 minutes. After fixing the wells were rinsed in PBS/BSA solution. The chambers were removed, retaining the gaskets on the slides. The anti-Mac-1 antibody was diluted 1:20 in the PBS/BSA solution, and 25 μl/well of the antibody solution was added to each well and incubated for 45 minutes at room temperature. After incubation, the wells were rinsed three times in the PBS/BSA solution. Twenty-five microliters of goat FITC-Anti-rat IgG (Boehringer Mannheim) diluted 1:50 in PBS/BSA solution was added to each well and incubated for 45 minutes at room temperature in the dark. The wells were rinsed three times in PBS/BSA solution and a final rinse in water was done. The gaskets were removed and a coverslip was mounted on the slide using mounting solution prepared using 9 parts of 2% 1,4 diazobicyclo(2,2,2)-octane in glycerol (Sigma, St. Louis, Mo.) that was dissolved at 70° C. and 1 part 0.2M Tris-HCL and 0.02% $NaN_3$ (pH 7.5) to prevent fading. Cultures of OC10A that had been treated with $10^{-8}$M 1a,25-dihydroxycholecalciferol and $10^{-7}$ dexamethasone were found contain Mac-1 positive cells.

F. Characterization of Bone Resorptive Activity

Bovine cortical bone wafers were cut on a Buehler 11-1180 isomet low speed saw (Buehler, Lake Bluff, Ill.). The slice were measured and sterilized using ethanol and ultraviolet light exposure overnight. The wafer sizes varied between 0.1–0.19 mm The wafers were rinsed in PBS and stored hydrated in growth medium at 37° C. in 5% $CO_2$. The wafers were placed in 8-chamber slides (Nunc), and cells were plated on the wafers at a density of $5 \times 10^4$ cells/well. The medium was changed every four days. On day 10, the medium was changed to low pH α-MEM with 0.7 g/L $NaHCO_3$, $10^{-8}$ 1α,25-dihydroxycholecalciferol and $10^{-7}$ dexamethasone added. On day 12 the medium was removed, trypsin/EDTA solution was added overnight, and the wafers were sonicated to remove the cells from the wafers. The wafers were rinsed in PBS and stained with 1% Toluidine Blue and 1% sodium borate for 1 minute. The excess stain was removed by washing with PBS followed by water. The wafers were viewed under an inverted scope at 10× magnification for quantitation of resorption pits using the Optimas Image Analysis program (Bioscan, Edmonds, Wash.). Results of the scanning microscopy demonstrate that OC10A cultures resorb bone.

EXAMPLE II

Preparation of an Osteoblast Cell Line

A. Harvesting cells from calavaria

Calvaria were removed from three p53 knockout mice (see Example IA) and placed in a 10 cc petri dish with 5 to 10 mls of growth medium (Table 1) containing 15% fetal calf serum. The calvaria were rinsed once in growth media. After rinsing, calvaria were placed in a Falcon centrifuge tube (Becton Dickinson Labware, Lincoln Park, N.J.) and minced using scissors. The minced bone was spun in a Beckman TJ-6 centrifuge (Beckman Instruments) at 1000 rpm for 10 minutes at room temperature. The bone was separated from the supernatant, and 3 ml of growth medium with 0.1% Type II collagenase (Sigma) was added to the minced bone pieces. The bone and collagenase mixture was incubated by shaking for 10 minutes at 37° C. After incubation, the supernatant was removed with a pipette, leaving bone pieces behind. The supernatant was placed in a 15 ml conical bottom Falcon centrifuge tube (Becton Dickinson Labware), and 3 ml of fetal calf serum was added to stop the collagenase digestion. The mixture was centrifuged at 1000 rpm for 10 minutes. After centrifugation, the cells were resuspended in 3 ml of growth medium with 15% fetal calf serum added to the medium. The collagenase digestion of the calvarial bone pieces was repeated five times, separating the supernatant from the bone pieces after each digestion. The bone pieces were washed five times in 15 ml of phosphate buffered saline (PBS) with 0.133 g/L calcium chloride-2H$_2$O and 0.1 g/L magnesium chloride-6H$_2$O and then placed in growth medium with 15% fetal calf serum. Cultures containing cells from the serial digestions and bone pieces were placed at 37° C. and 5% CO$_2$ in growth medium. The cells were seen to crawl from the bone pieces after approximately 2–4 days.

The cells were replated at a clonal density of 1 cell/well in a 96-well petri dish containing growth medium. Single colonies were replica plated, with one replicate petri dish of the colony maintained as a cell line and the other used for characterization. Characterization included testing for the presence of alkaline phosphatase, Von Kossa staining (to visualize in vitro and in vivo mineralization), Alizarin Red S staining (to visualize in vitro mineralization), Goldner staining (to visualize in vivo mineralization), PTH induction of cAMP and osteocalcin expression.

B. Expression of Alkaline Phosphatase

Expression of alkaline phosphatase as a marker of osteoblast phenotype was assayed using a diagnostic kit (Sigma, St. Louis, Mo.) according to manufacturer's specifications. Briefly, cells are affixed with a citrate/acetone/formaldehyde fixative (Sigma) to slides and then incubated in a solution containing naphthol AS-MX phosphate. In the presence of phosphatase activity, naphthol AS-MX is liberated and immediately coupled with a diazonium salt, forming an insoluble, visible pigment at the sites of phosphatase activity. Three cell lines, designated 2-29, 2-45 and CCC-4 stained positive for alkaline phosphatase stain red.

C. cAMP induction by PTH

The ability of PTH to induce cAMP production in cell lines 2-29, 2-45 and CCC-4 was measured using a Scintillation Proximity Assay kit (Amersham, Arlington Heights, Ill.) according to the manufacturer's specifications. Briefly, 1×10$^5$ cells/well were plated into the wells of a 24-well plate (American Scientific Products, Chicago, Ill.) and grown for 2 days in selection medium. PTH and forskolin were prepared in α-MEM, 10% fetal calf serum and 10 μM IBMX.

The growth medium was replaced with 200 μl/well of growth medium containing agonist, either PTH (bovine fragment 1-34, Sigma) or forskolin. The cells were incubated with the agonists for 10 minutes at 37° C. in 5% CO$_2$. Following incubation, 800 μl of boiling water was added to each well. After 15 minutes the supernatants were collected and diluted 1:5 or 1:40 in acetate buffer (cAMP [$^{125}$I] Scintillation Proximity Assay System (Amersham)). Samples were acetylated using triethylamine and acetic anhydride according to the protocol provided by the manufacturer.

A 100 μl aliquot of each acetylated sample was combined with 75 μl of $^{125}$I-cAMP, 75 μl anti-succinyl cAMP antisera and 75 μl of donkey anti-rabbit IgG coupled SPA beads (all assay solutions provided in the cAMP [$^{125}$I] Scintillation Proximity Assay System (Amersham)) in a well of a Dynatech MICROLITE 2 plate. The trays were sealed and incubated overnight with continuous shaking on a rotary platform shaker at 200 rpm. The samples were counted in a Packard Top Count Microplate Scintillation Counter (Packard Instrument Co., Meriden, Conn.). A standard curve of 2-128 fmol acetylated cAMP was also run. Total $^{125}$I-cAMP bound and nonspecific binding was also determined.

|       | –PTH | +PTH  |           |
|-------|------|-------|-----------|
| 2-29  | 54   | 1155  | 22-fold   |
| 2-45  | 45   | >8000 | >176-fold |
| CCC-4 | 34   | 1280  | 37-fold   |

The results clearly demonstrate that PTH induced cAMP production in cell lines 2-29, 2-45 and CCC-4.

D. Characterization of Bone Mineralization

Mineralization was induced by the addition of 10 mM β-glycerophosphate and 50 μg/ml ascorbic acid to the culture medium. Cells were grown in the supplemented medium for 1–3 weeks. The medium was removed from the cells, and the petri dish was rinsed in PBS. Cells were fixed with Z-FIX (Anatech Ltd.). After fixing, the cells were rinsed three times with distilled water. A solution of five grams of silver nitrate in 100 ml of water was added to the cells at 1 ml/well and placed in the dark for 5 minutes. After incubation, the cells were rinsed three times in distilled water. A solution of 5 g of sodium carbonate, 75 ml distilled water and 25 ml of 38% formaldehyde was added to each well at 1 ml/well for 1 minute. The cells were rinsed 2–3 minutes with tap water. Farmer's Reducer (0.2 ml of 10% sodium thiosulphate, 1.0 ml of 0.1 g/ml potassium ferricyanide, 20 ml of water) was added at 1 ml/well for 1 minute. The cells were rinsed 10 minutes with tap water. Cells were scored visually for silver staining.

Alizarin Red S staining was done by rinsing cells with PBS and fixing the cells with Z-FIX for 10 minutes. The cells were rinsed several times in distilled water. Alizarin Red S stain (Sigma) was prepared at a concentration of 0.2 gr/10 ml PBS and used to stain cells in the culture dishes for 5 minutes. The excess stain was removed by rinsing with distilled water.

The ability of cells to mineralize bone in vivo was measured by placing diffusion chambers in mice. Diffusion chambers (Millipore, Bedford, Mass.) were filled with approximately $5\times10^6$ cells/130 μl PBS/chamber. Swiss-webster mice (B&K Universal, Seattle, Wash.) were anesthetized with ketamine and xylazine. Chambers were surgically implanted intraperitoneally and closed using silk interrupted sutures. Skin clips were used to close the skin layer. After 9 weeks mice were sacrificed, diffusion chambers were fixed, processed and embedded in plastic, and histology was performed to measure bone mineralization by Von Kossa staining as described above and Goldner's trichrome stain.

The diffusion chamber samples were prepared by fixing the chambers in 10% neutral buffered formalin (Anatech) for 24 hours at 4° C. The chambers were processed in a BIP 2000 Automatic Tissue Processor (Miles Scientific, Elkhardt, Ind.). The processed chambers were infiltrated at 4° C. with a first solution of 15 mls of 70% methyl methacrylate, 30% n-butyl methacrylate in a scintillation vial placed on an orbital shaker. The chambers were embedded by placing the vials at 4° C. and covered in a solution containing 70% methyl methacrylate, 30% n-butyl methacrylate, 1:20 volume methanol, 3% benzoyl peroxide and 1:600 volume n,n-dimethylaniline and placed under vacuum in a glass dessicator. The process was repeated for a second embedding.

The embedded slides were sectioned on a Reichert-Jung Autocut microtome, and 5 μm sections were mounted on glass slides. The slides were stained using Von Kossa stain and Goldner's trichrome stain. Sections were placed in Mayer's hematoxylin (Sigma) for 1 hour and rinsed in tap water for 1 minute. The sections were covered with 0.25% ammonium hydroxide in water for 45 seconds and rinsed in tap water for 1 minute. The sections were covered with Ponceau/acid fuchsin (prepared using 0.13 g of Ponceau de Xylidine (Sigma), 0.03 g of acid fuchsin, 0.2 ml of glacial acetic acid and 100 ml of distilled water) for 10 minutes, transferred to 1% glacial acetic acid for two rinses, and rinsed once in 0.5% glacial acetic acid. The sections were transferred to phosphomolybdic acid/orange (prepared using 5 g of phosphomolybdic acid, 100 ml of distilled water and 2 g of orange G) for 10 minutes, and rinsed twice with 1% glacial acetic acid and once in 0.5% glacial acetic acid. Sections were placed in light green stain (prepared using 0.3 g of light green stain (Sigma), 0.2 ml of glacial acetic acid and 100 ml of distilled water) for 10 minutes. Sections were rinsed twice in 1% glacial acetic acid, followed by rinses in 70% ethanol and 95% ethanol. The sections were transferred twice into absolute ethanol for 2 minutes, and then transferred three times into xylene for 2 minutes.

The cell lines designated 2-29, 2-45 and CCC-4 all showed detectable mineralization in vitro 5–8 days after the addition of β-glycerophosphate and ascorbic acid. In vivo mineralization was demonstrated for all three cell lines six weeks after implantation of the diffusion chambers.

D. Expression of Osteocalcin

Osteocalcin expression was measured using a radioimmune assay kit from Biomedical Technologies, Inc. (Stoughton, Mass.) according to the manufacturer's specifications. Briefly, media samples were collected from cell lines and prepared either undiluted or diluted 1:5. $^{125}$I osteocalcin is added, followed by goat anti-mouse osteocalcin. The complex was precipitated using donkey anti-goat antibodies and centrifuged. The radioactivity in the resulting pellet was measured on a gamma counter, and osteocalcin secretion was calculated as the ng of osteocalcin present in the medium per well.

| | osteocalcin (ng/well) | |
|---|---|---|
| cell line | −β-glycerophosphate and ascorbic acid | +β-glycerophosphate and ascorbic acid |
| 2-29 | 58 | 1050 |
| 2-45 | 114 | 1775 |
| CCC-4 | 306 | 4800 |

Results clearly demonstrate that in the presence of β-glycerophosphate and asorbic acid, osteocalcin was secreted in cell lines 2-29, 2-45 and CCC-4.

Although the foregoing invention has been described in some detail by way of illustration and example for purposes of clarity and understanding, it will be obvious that certain changes and modifications may be practiced within the scope of the appended claims.

We claim:

1. A method of preparing immortalized cell lines of an osteoclast lineage or of an osteoblast lineage comprising the steps of:

culturing bone tissue or bone marrow tissue from a p53 growth suppressor gene deficient mouse in a growth medium isolating component cells from the cultured tissue;

assaying a least a portion of the isolated component cells for expression of a set of differentiation markers expressed by a cell of an osteoclast or osteoblast lineage thereby identifying a subset of said isolated cells; and selectively culturing said subset of cells expressing said set of differentiation markers wherein said subset of cells are osteoclast lineage or osteoblast lineage cells and said set of differentiation markers include Mac-1 expression and non-specific esterase expression for osteoclast lineage cells and include alkaline phosphatase expression, parathyroid hormone-induced cAMP expression, osteocalcin expression, and bone mineralization capacity for osteoblast lineage cells.

2. The method of claim 1, wherein said portion of the isolated component cells comprise osteoclast lineage cells, which are stimulated to differentiate prior to the step of assaying.

3. The method of claim 2, wherein the cells of said subset are osteoclast precursors.

4. The method according to claim 1, wherein the tissue is calvarial bone and the subset of cells are osteoblast lineage cells.

5. The method according to claim 1, wherein the tissue is bone narrow.

6. The method according to claim 5, wherein the cells of said subset are osteoblast lineage cells.

7. The method according to claim 5, wherein the cells of said subset are osteoclast precursors.

8. An immortalized p53-deficient mouse osteoblast lineage cell line wherein cells of said cell line exhibit a set of differentiation markers including alkaline phosphatase expression, parathyroid hormone-induced cAMP expression, osteocalcin expression, and bone mineralization capacity.

9. An immortalized p53-deficient mouse osteoclast lineage cell line wherein cells of said cell line exhibit a set of differentiation markers including Mac-1 expression and nonalkaline phosphatase expression and wherein upon induction of cells of said cell line to differentiate said cells produce mouse osteoclast cells, said osteoclast cells exhibiting a set of differentiation markers including calcitonin receptor expression, tartrate resistant acid phosphatase expression, and bone resorptive activity.

10. Mouse osteoclast cells characterized by a set of differentiation markers including calcitonin receptor expression, tartrate resistant acid phosphatase expression, and bone resorptive activity produced by inducing the cell line of claim 9 to differentiate.

* * * * *